(12) United States Patent
Whitehurst

(10) Patent No.: US 6,461,866 B1
(45) Date of Patent: Oct. 8, 2002

(54) IN VITRO PHOTODYNAMIC THERAPY USING NON LASER LIGHT

(75) Inventor: Colin Whitehurst, Manchester (GB)

(73) Assignee: Photo Therapeutics Limited (GB)

( * ) Notice: Subject to any disclaimer, the term of this patent is extended or adjusted under 35 U.S.C. 154(b) by 0 days.

(21) Appl. No.: 09/711,891

(22) Filed: Nov. 15, 2000

Related U.S. Application Data

(62) Division of application No. 09/020,317, filed as application No. PCT/GB93/02187 on Oct. 22, 1993, now Pat. No. 6,171,332, which is a continuation of application No. 08/256,059, filed on Aug. 24, 1994, now Pat. No. 5,843,143.

(30) Foreign Application Priority Data

Oct. 23, 1992 (GB) .............................. 9222245

(51) Int. Cl.$^7$ .................................. C12N 5/00
(52) U.S. Cl. ................. 435/325; 435/173.1; 435/173.4; 607/88
(58) Field of Search .............................. 435/325, 173.4, 435/173.1; 607/88

(56) References Cited

U.S. PATENT DOCUMENTS

| | | |
|---|---|---|
| 4,298,005 A | 11/1981 | Mutzhas |
| 4,444,190 A | 4/1984 | Mutzhas |
| 4,686,986 A | 8/1987 | Fenyo |
| 4,860,172 A | 8/1989 | Schlager |
| 4,874,361 A | 10/1989 | Obagi |
| 5,000,752 A | 3/1991 | Hoskin |
| 5,259,380 A | 11/1993 | Mendes |
| 5,320,618 A | 6/1994 | Gustafsson |
| 5,344,418 A | 9/1994 | Ghaffari |
| 5,344,433 A | 9/1994 | Talmore |
| 5,344,434 A | 9/1994 | Talmore |
| 5,405,368 A | 4/1995 | Eckhouse |
| 5,445,634 A | 8/1995 | Keller |
| 5,556,992 A * | 9/1996 | Gaboury et al. |
| 5,599,831 A * | 2/1997 | Poretz et al. |
| 5,637,451 A * | 6/1997 | Ben-Hur et al. |

FOREIGN PATENT DOCUMENTS

| | | |
|---|---|---|
| EP | 023 311 | 2/1981 |
| EP | 0 052 765 | 10/1981 |
| EP | 0 406 454 | 1/1991 |
| EP | 485 864 | 5/1992 |
| FR | 2 511 877 | 3/1983 |
| GB | 2 212 010 | 7/1989 |
| WO | 90 11105 | 10/1990 |
| WO | WO 91/15264 | 10/1991 |
| WO | 92 13597 | 8/1992 |

OTHER PUBLICATIONS

Physics in Medicine and Biology, vol. 31, No. 4, Apr. 1986—Wilson et al., "The physics of photodynamic theory", p. 334, paragraph 3 "Light sources for PDT", p. 335, Table 2.

\* cited by examiner

*Primary Examiner*—Leon B. Lankford, Jr.
(74) *Attorney, Agent, or Firm*—Sterne, Kessler Goldstein & Fox P.L.L.C.

(57) ABSTRACT

A cosmetic method of treatment of dermatological conditions, particularly portwine stains, tattoos or psoriasis, which includes irradiating the affected area with an incoherent high intensity non-laser light beam having an intensity greater than 0.075 watts per square centimeter, the light beam having only a bandwidth in the range 0 to 30 nm. The method can include delivery of the light beam by optic fiber bundle by pulsed or non-pulsed light. The method can also include the introduction of a drug into the body undergoing the treatment, wherein the drug is activated by light of a particular wavelength.

5 Claims, 4 Drawing Sheets

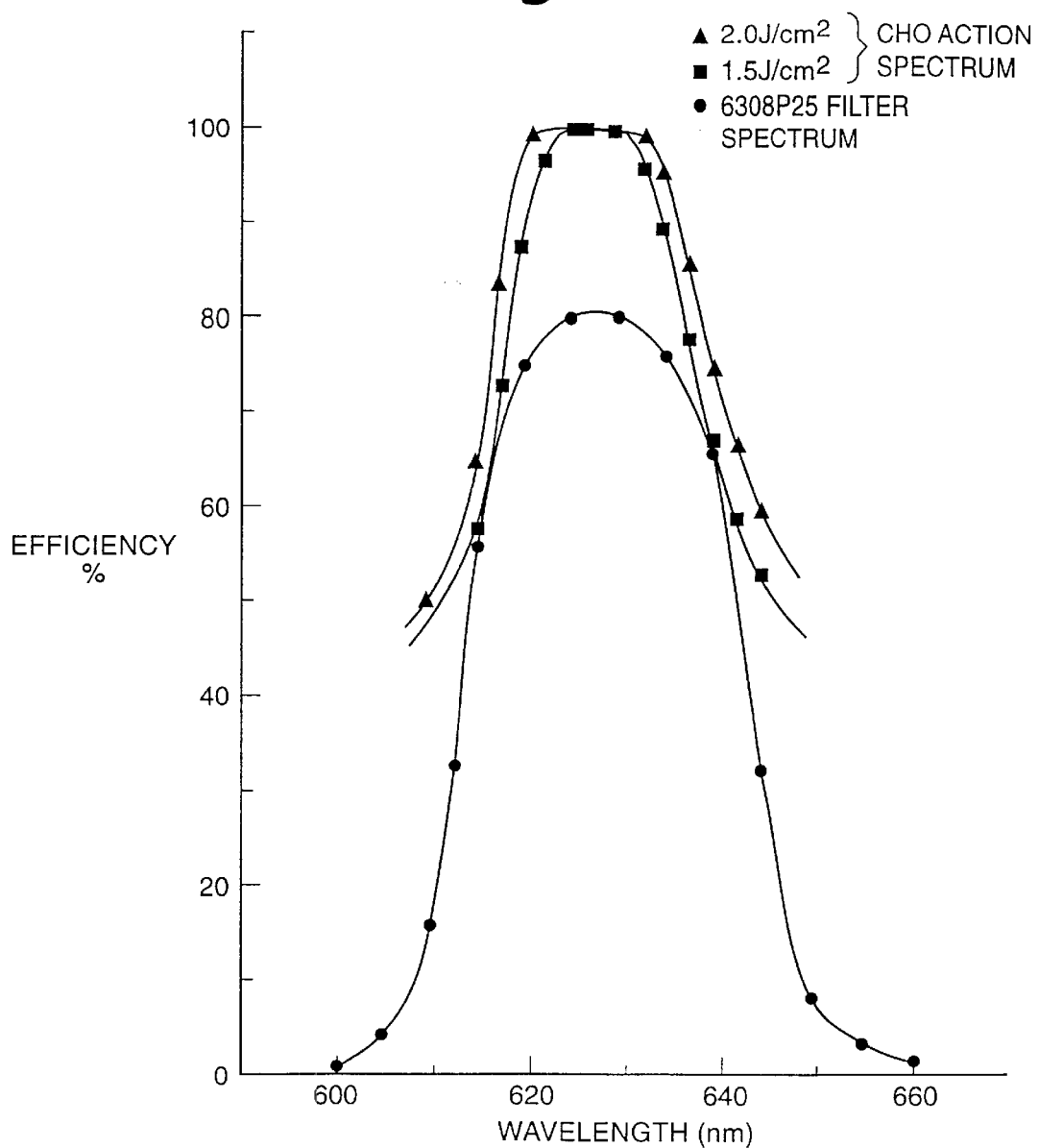

IN VITRO PHOTODYNAMIC THERAPY USING NON LASER LIGHT

This application is a divisional of application 09/020,317 filed Feb. 9, 1998 now U.S. Pat. No. 6,171,332, which is a continuation of application 08/256,059, filed Aug. 24, 1994, now U.S. Pat. No. 5,843,143 which is a national stage entry of PCT/GB93/02187 filed Oct. 22, 1993.

This invention relates to a light source which is an incoherent or non-laser light source for use primarily but not exclusively in medical applications.

Lasers have widespread uses in the treatment of the human or animal body, which uses may be of a therapeutic and/or cosmetic nature. For example, laser light can be used to kill cancer cells or for treatment of portwine stains and removal of tattoos. However, medical lasers tend to have many disadvantages. Firstly, some medical lasers for certain requirements can cost up to a one hundred and forty thousand pounds or more and may require very bulky power supplies and/or bulky transformers in addition to involving complex or inconvenient cooling arrangements. Additionally, the power consumption by the laser may be very high and the laser itself may not be user friendly, for example, some lasers may require a one and a half hour warm-up time before they can be used in certain applications and may have a similar shut-off period. Often, the laser itself may be a far more sophisticated piece of equipment than is actually required for a particular task and therefore may be over suited to the task in hand. Some medical applications do not in fact require the critically offered by a laser although other acceptable light sources do not seem to have been developed to be used instead of a laser in such applications.

Non-laser light sources have been developed for medical applications but such proposals have tended to be inefficient and generally unsuitable for the task in hand. For example, a paper from the *Journal of Photochemistry and Photobiology B: Biology* 6 (1990) 143–148 on Photodynamic Therapy with Endogenous Protoporphyrin reports the use of a 500 watt filament light source for irradiation of cancerous cells. The light source was varied from 150 to 300 watts per square centimetre but spread over a very wasteful large bandwidth greater than 100 nm. The filtering tended to be inefficient and unsuitable giving rise to tissue damage from thermal effects.

Another proposal is discussed in the "Phototherapy of Human Cancers" in an article entitled Porphyrin Localisation and Treatment of Tumors, pages 693–708, 1984 Alan R. Liss, Inc. This article discusses the use of a filtered incandescent lamp having a 1000 watt filament source which is water cooled. The size of the apparatus itself is large and tends to be inefficient also entailing considerable risk of skin damage because of high flux density.

It is an object of at least some embodiments of the present invention to provide an incoherent or non-laser light source which at least alleviates one or more of the aforementioned, or other, disadvantages associated with lasers or which is more suited to the particular task in hand than a laser.

According to a first aspect of the present invention there is provided an incoherent or non-laser light source comprising a high intensity lamp, a bandpass filter and focusing means arranged to yield a light beam having an output intensity greater than 0.075 watts per square centimetre for a bandwidth in the range 0 to 30 nm and preferably in the range 0 to 25 nm.

Usually, the output intensity of said light source will be greater than 1 watt per square centimeters for a bandwidth usually in the range 20 to 25 nm.

Preferably, the light source is tunable over a range of at least 350 to 700 nm and usually over a range of 250 to 1100 nm.

Preferably, the output beam is focused sufficiently so that light can be delivered by way of an optical fibre means or bundle to its point of action and said beam may be focused down to a 6 mm or less diameter.

In one embodiment of the present invention, the light source may be arranged to yield a beam with an output intensity of 6 watts per square centimetre at a bandwidth of 20 to 25 nm. The lamp may be a metal halide lamp.

Alternatively, the lamp may be a high intensity high pressure xenon, short arc lamp or any lamp producing intense light over a continuous spectrum. It is envisaged that an extended light source such as a filament would not produce the required intensity due to filament diversions. In this context a short arc lamp would appear to be the best option yet available and may be for example of only 300 watts or 500 watts, but preferably less than 1 kw due to heat output and and arc length. Preferably, the beam divergence of the lamp is very low, for example in the order of 4° FWHM with a beam stability preferably in the order of 1%. Preferably, the lamp is adapted (for example by coating various parts thereof) to remove ultra-violet (UV) radiation from the light beam emerging from a lamp window.

The focusing means, preferably, comprises an aspheric lens and said lens is preferably anti-reflection coated.

The bandpass filter may be at least 50% of 65% efficient and is preferably 80% efficient or greater (e.g. 91%) for light within the transmission bandwidth.

A dichroic "hot mirror" may be provided to remove infra-red radiation from the beam.

A variable attenuator grill may be provided in order to vary the power output of the light source.

The light source is, preferably, provided with a readily interchangeable output window incorporating a connection matching a connection on a fibre optic bundle. In this manner the window can be interchanged for one having a different sized connection for a different sized fibre optic bundle. The output window may be provided in a screw cap.

A preferable embodiment of the present invention provides a portable light source. The size of the light source may have overall dimensions of 15" by 10" by 6". The light source may be provided with a power supply connected to the lamp (preferably a xenon arc lamp or metal halide lamp). A cooling fan is preferably provided at the rear of the lamp. The light source may comprise a control shutter positioned directly in front of the lamp (in an alternative arrangement the shutter may be provided inbetween the bandpass filter and the aspheric lens) and followed by a dichroic "hot mirror" or other means to remove infra-red radiation and then by the bandpass filter, aspheric focusing lens and variable attenuation means. The light source is preferably provided with a control panel at the front thereof in order to operate the control shutter for timed exposure as well as perhaps incorporating manual override switches. The light source is, preferably, tunable by replacement of the bandpass filter and/or dichroic "hot mirror". If it is desired for the emergent beam to be in the infra-red region for example for treatment of hyperthermia the "hot-mirror" can be replaced with a cold mirror to filter out the visible light. Additionally, the bandpass filter may be changed for one allowing light of a greater bandwidth (for example 100 or 200 nm) to pass through.

Further according to the present invention there is provided a non-laser light source comprising one or more of the following features:

(a) means for supplying a (monochromatic) light beam suitable for delivery into a fibre optic bundle, said light beam having a sufficient intensity for a bandwidth useful in PDT (photodynamic therapy) and/or (b) in cosmetic methods of dermatological treatment, means for supplying a light beam of an intensity of at least 100 mw per square centimetre for a bandwidth in the range 20 to 25 nm, (c) means for providing a beam of intensity greater than 0.075 watts per square centimetre which is tunable in the range of 250 to 1100 nm, (d) said light source being portable and air cooled, (e) means for delivering a (monochromatic) light beam to fibre optic bundles having different connector sizes, (f) a bandpass filter of 60 to 90% efficiency or greater in a narrow nanometer range (for example less than 25 nm), (g) facility for interchanging bandpass filters of different characteristics, (h) said non-laser light source being suitable for medical applications in particular treatment of tumours and/or delivery of light suitable for photo-inactivation of cancer cells containing a drug having an absorption level in a narrow nanometer bandwidth, for example lying in the range 20 to 25 nm.

Further according to the present invention there is provided a method of in vitro PDT, said method comprising delivering non-laser light of a sufficient intensity to kill cancer cells, preferably of an intensity greater than 0.075 $W/cm^2$ and usually 10 to 200 $mW/cm^2$ for a bandwidth in the range 20 to 25 nm.

Further according to the present invention there is provided a cosmetic method of treatment of dermatological conditions, for example comprising removal of portwine stains, tattoos or psoriasis, using an incoherent light beam from a non-laser light source emitting a high intensity beam having an intensity greater than 0.075 watts per square centimeters for a bandwidth in the range 0 to 25 nm, said beam preferably being deliverable by an optic fibre bundle, and said method preferably comprising pulsing said beam. For removal of portwine stains wavelengths of 575 nm may be used and for removal of tattoos wavelengths of 620 nm may be used. The method may involve the introduction of a drug into the body undergoing cosmetic treatment, said drug being selectively activated by light of a particular wavelength.

According to a further aspect of the present invention there is provided, a non-laser light source suitable for medical applications, which source is tunable over a bandwidth of 350 to 700 nm (preferably over a bandwidth of 250 to 1100 nm) and which is capable of focusing a light beam for fibre optic delivery at an intensity of 100 $mW/cm^2$ for a bandwidth of 25 nm or less.

Preferably, said light source is capable of focusing a beam at an intensity of up to 9 $W/cm^2$ for a bandwidth of 25 nm or less.

Usually, the light source will be provided with a timed exposure facility and it is advantageous for the beam to be as intense as possible below thermal dosage and hyperthermia limits (a few 100 $mw/cm^2$) since this will reduce the exposure time required.

An embodiment of a light source in accordance with the present invention will now be described by way of example only, with reference to the accompanying drawings in which:

FIGS. 2a, 2b, 2c show graphical data related to in vitro work, and

Figure 1:
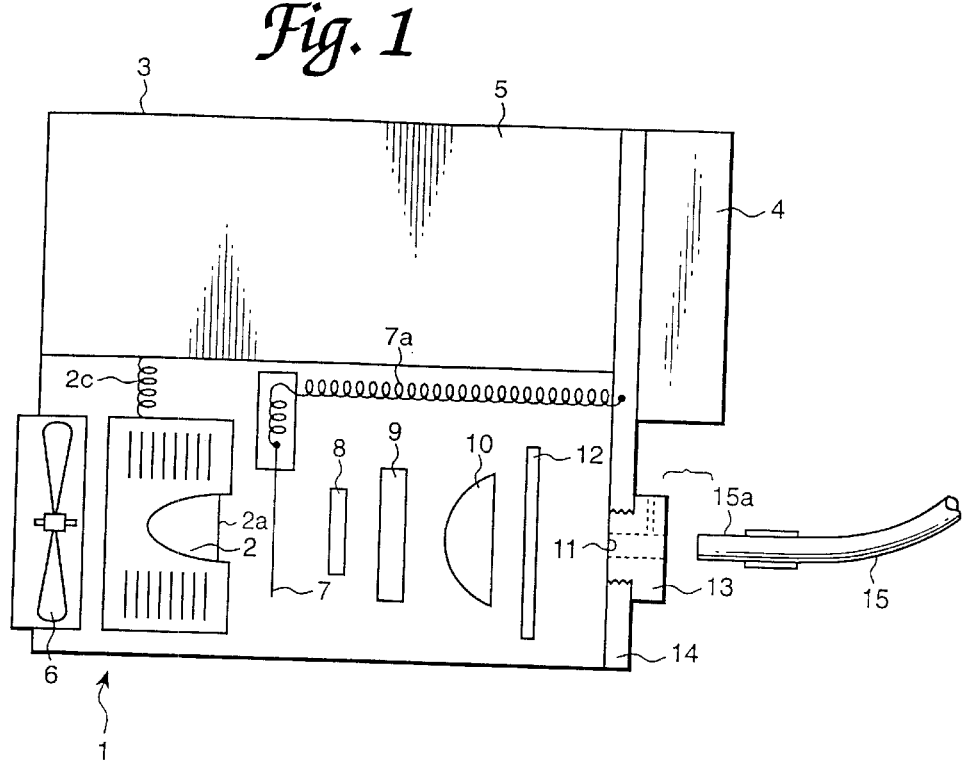
FIG. 1 shows a much simplified schematic over view of the light source.

The FIGURE shows a high intensity incoherent or non-laser light source 1 in schematic form. Light source 1 includes a lamp 2 which may be a high intensity, high pressure, xenon, short arc lamp (for example of 300 or 500 watts output) which would normally produce broadband ultra-violet, visible and infra-red radiation. Such a lamp has a beam divergence in the order of 4° FWHM and a beam stability in order of 1%. Such a lamp is marketed by ILC Technology of Sunnyvale, Canada. In this embodiment the lamp 2 is provided with a rear internal lamp reflector (not shown) and has a front window 2a which is a single crystal, sapphire window. The reflector and window 2a are provided with coatings selected to remove ultra-violet radiation from the emergent light beam from the window 2a. Removal of the ultra-violet radiation prevents harmful ozone production. The xenon lamp 2 is provided with other various components of the light source in an exterior casing 3 provided with a front control panel 4. A power supply unit 5 is provided to power the lamp 2 via electrical connection 2c and a rear cooling fan unit 6 is provided to cool the whole apparatus 1. A solenoid activated control shutter 7 is provided in front of the window 2a of the lamp and this control shutter is activated by a suitable control switch (not shown) provided on the control panel 4, said control shutter 7 being connected thereto by way of electrical connection 7a. Thus, the control shutter can be activated so that the light source can administer timed doses of 0 to 9999 seconds covering all medical exposures required. Manual operation and a manual override to terminate a time exposure is also provided in the light source 1 which is operable from the control panel 4. The control shutter 7 is operated by an inbuilt special purpose timer/controller.

In this embodiment of the apparatus 1, a Dichroic "hot mirror" 8 is positioned in front of the control shutter 7 in the beam path and this acts to remove intra-red radiation from the beam passed by the control shutter 7 resulting in a relatively smooth visible broadband beam in the range of 350 to 700 nm bandwidth at 50 mW/nm. The emergent beam from the "hot mirror" 8 impinges next upon a dielectrically blocked, high temperature bandpass filter 9 which selectively filters the light beam to produce an emergent beam of a much narrower bandwidth, preferably, in the order of 20 to 25 nm. Most importantly, in this example the bandpass filter is 80% efficient at filtering the light lying in said bandwidth in order to enable a sufficiently intense beam to be produced by the light source 1 which is suitable for various medical applications. Such a bandpass filter may be obtained from Omega Optical c/o Glen Spectra in Middlesex.

The beam emergent from the bandpass filter is in the order of 2 to 2.5 cm diameter and is then focused by an anti-reflection coated F1 aspheric lens 10 which focuses the beam down to about 6 mm diameter at the output window 11 of the light source 1. The coating itself may be a magnesium fluoride coating which reduces losses of for example 10 to 15% down to only 3% in energy of the beam. The lens 10 is a tight variable angle lens and can be obtained from Ealing Electro-Optics of Waterford.

A variable attenuator means in the form of grill 12 is provided, said grill being a plate which is rotatable about its own axis in order to vary the intensity of the output beam. Areas of the plate are provided with apertures (not shown) graduated in size according to the angle to which the plate is rotated to allow more or less of the beam through in order to vary the power of the output beam between zero and full power. Such a method of varying the power output of the output beam is preferable to using a control on the lamp 2 itself and should extend the working life of the lamp.

The output window 11 is provided in a screw-cap 13 which can be fitted into the bulkhead 14 of the light source 1. The screw-cap 13 is provided with a central tubular aperture matched to the connection end 15a of an optical fibre bundle 15 of 5 mm or less diameter and of 1 to 4 metres or greater in length. Thus, the lens 10 is designed to minimise optical losses and spherical abberation and focus the beam sufficiently to enable delivery of the light to its point of action by way of an optical fibre bundle. Such a fibre bundle may be obtained from Eurotec Optical Fibres, Doncaster.

It is envisaged that the light source as described will be invaluable in all types of medical applications where hitherto only a laser has been available. In particular the light source (which may be thought of as mimicking a laser) as shown is self-contained and portable, the external dimensions of the casing being in the order of 15" by 10" by 6", said light source being lightweight and robust unlike lasers required for similar medical applications. Additionally, the light source requires a very low electricity consumption particularly in comparison with a laser.

The light source 1 as shown in the FIGURE can be arranged to yield a beam output from the cap 13 having an intensity of 3 watts per square centimetre for a bandwidth of 20 to 25 nm and if the xenon lamp 2 is replaced by a metal halide lamp it is believed that a beam intensity of 9 watts per square centimetre can be achieved for the same bandwidth. Delivery of light from the light source 1 to the point of action may be by way of the fibre bundle 15 and there may be considerable losses in intensity of the beam down the optical fibre bundle perhaps in the order of 50%. Losses can be improved by the choice of fibre bundle. In any event, the intensity of light delivered by the light source as described at the distal tip of the fibre bundle 15 may be in the order of 30 to 40 m Watts per nanometer over a bandwidth of 20 to 25 nm and this has been proven very effective in certain medical applications where a laser would be required. For example, in the area of photodynamic therapy (PDT) there has been proven photo-inactivation of cancerous Chinese Hamster Ovary (CHO) cells in vitro with the haematoporhyrin derivative HpD with the impinging light on the cells being in the visible band at 630±12 nm. Test results have indicated a similar cell kill efficiency and quality of kill to that achieved by current medial lasers. Accordingly, some results obtained by the Applicant will now be discussed with reference to FIGS. 2a to 2c and 3a,3b.

IN VITRO PDT TEST RESULTS

In vitro work carried out using Chinese hamster ovary (CHO) cells incubated with 10 pg/ml HpD for 24 hours. Irradiation was centered on 630±12 nm for three light sources, namely a high intensity continuous wave (CW) lamp (non-laser light source in accordance with the present invention using 300 W Xenon lamp), secondly a continuous wave 20 W argon ion pumped dye laser and pulsed 10 W copper vapour pumped dye laser, all with fibre delivery. Light doses ranged from 0 to 2.5 $J/cm^2$ with light fluences ranging from 20 to 200 $mW/cm^2$. A light only control was taken at 275 $mW/cm^2$ for energy doses of 0 to 100 $J/cm^2$. Following irradiation, cells were plated out, stained and counted for survival.

Figure 2A:
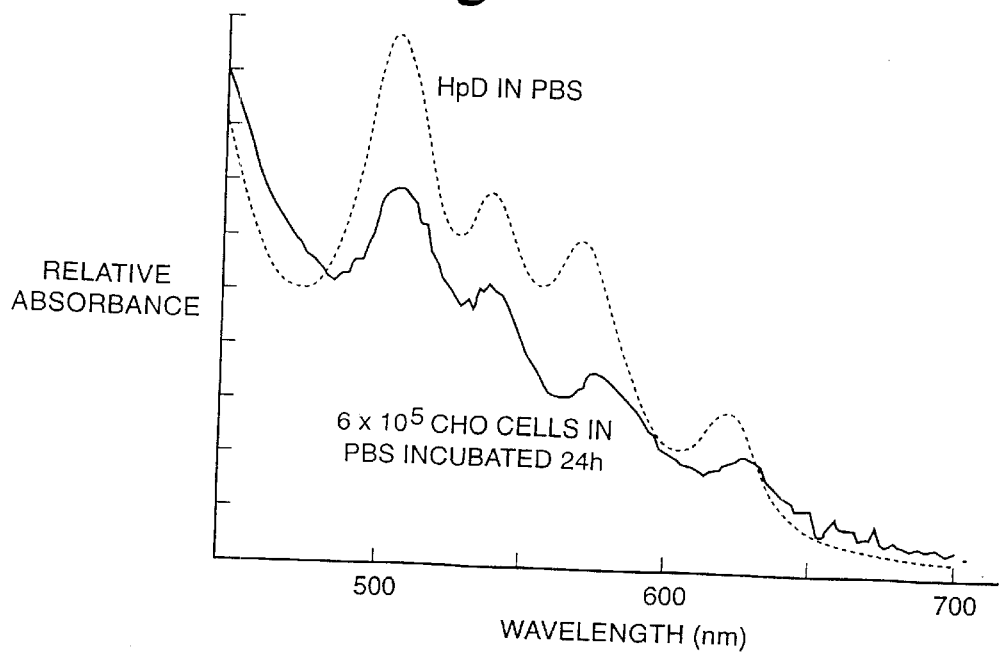
Figure 2C:
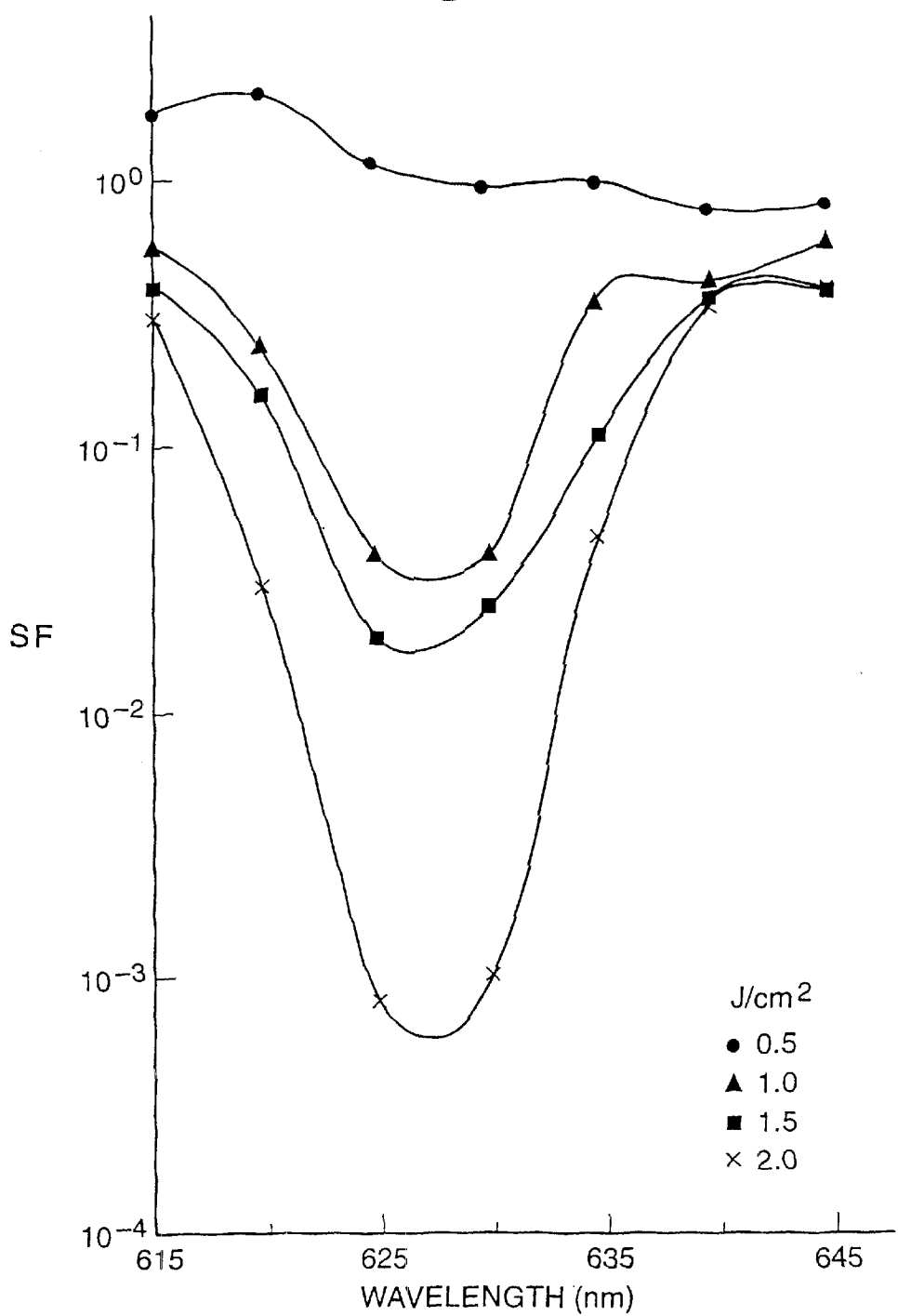

FIGS. 2a, 2b, 2c show photosensitiser (HpD) absorption spectrum, cell kill efficacy spectrum and overlapping HpD/lamp spectra. PBS refers to phosphate buffered saline; S.F. means survival fraction.

Figure 3A:
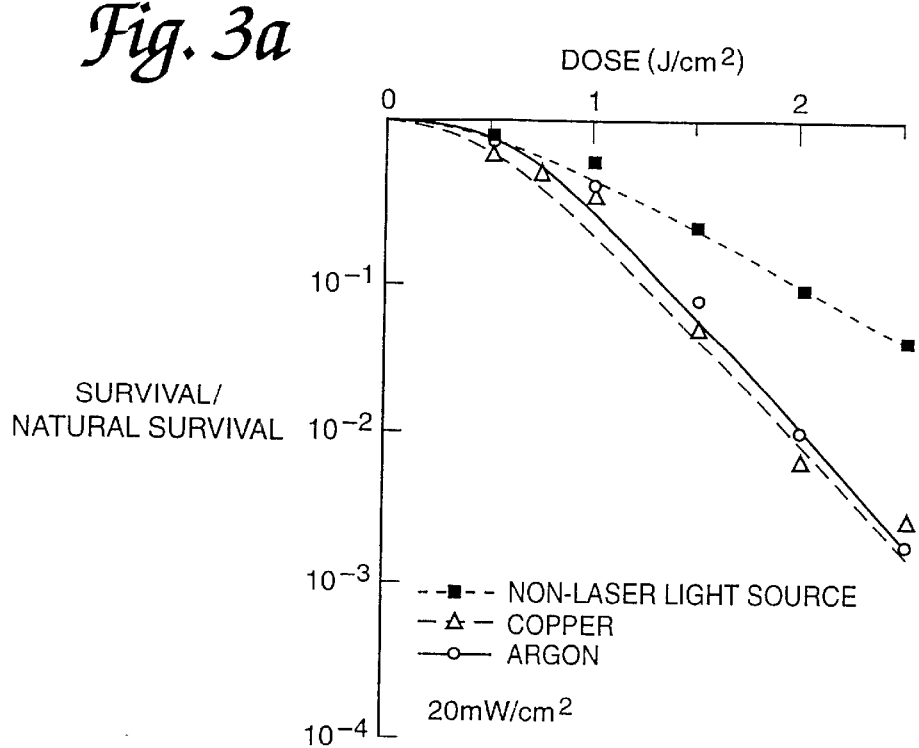
FIGS. 3a, 3b show test results of the Applicant related to in vitro work.
Figure 3B:
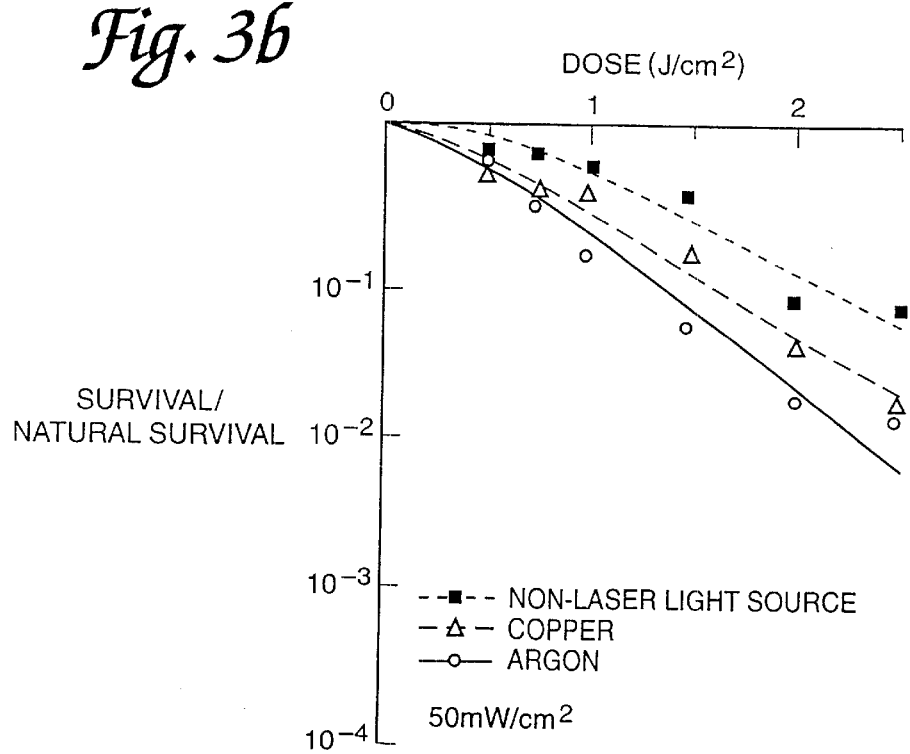

FIGS. 3a, 3b show cell survival curves obtained at 20 & 50 $mW/cm^2$ respectively with highest kill efficiency achieved by the argon ion laser, followed by the copper vapour laser. The lamp kill efficiency of the light source in accordance with the present invention, though similar to the lasers (approx 70%) would be increased by reducing its emission bandwidth from 30 nm.

In PDT a drug (such as HpD) is introduced into cancerous cells, which drug absorbs light in a narrow bandwidth (for example 20 to 25 nm) only and the light source is set up to emit a beam only in that required bandwidth which for HpD is 630±12 nm. Other drugs only absorb light of different wavelengths but once again in a narrow bandwidth and it is an easy matter to arrange for the light source to emit light at a different wavelength but still within the same narrow bandwidth merely by changing the bandpass filter 9. In the arrangement as shown, the bandpass filter 9 would have to be removed from the light source and a new one inserted in its place but in a modification it is possible that multiple bandpass filters could be incorporated into a movable frame (for example a rotatable disc) in order for a different bandpass filter filtering out light of a different wavelength (but within the same narrow bandwidth if required) to be quickly and easily presented in the beam path.

In fact, the drug HpD has further selective absorption bands at different bandwidths and different bandpass filters can be matched to these bandwidths. For example, HpD has an absorption band in the blue region and in the U.V. region at about 400 nm and at about 500, 540 and 570 nm. However, the shorter the wavelength the less the penetration. More efficient blue light could be used for typographical or dermatological work (penetration approximately 1 or 2 mm).

However, for large tumours or interstitial work 5 to 10 mm penetration is usually required and therefore light of longer wavelength is required.

Most importantly, the selection of a suitable bandpass filter from a range of bandpass filters provides a unique tuning facility for the light source. This feature itself is a very significant advantage over lasers which are set to emit light of one wavelength only and do not have such a tuning capacity. Thus, different medical lasers are required for different medical applications where different wavelengths of light are required. With the light source 1 in accordance with the present invention the same piece of apparatus can be used for different medical applications requiring different wavelengths of light to be employed (merely by changing the bandpass filter), once again providing an enormous cost advantage and convenience over medical lasers.

Thus, the light source 1 can provide variable bandwidth optical emissions centred on any wavelenths from 250 nm to 1100 nm deliverable by optical fibre of sufficient intensity to initiate either in vitro or in vivo external/interstitial photodynamic therapy (PDT). If it is desired to deliver light outside of the visible region i.e. in the infra-red region between 700 nm and 1100 nm or so this can be done by the light source 1 merely by changing the dichroic mirror 8 for a cold mirror which blocks the visible light but allows a light through in the bandwidth region 700 to 1100 nm. Therefore, the tunability of the light source extends to the infra-red for Hyperthermia applications. Light of longer wavelength is generally required for such applications since a better penetration can be achieved but a narrow bandwidth is not usually required. The bandwidth may be 200 or even 300 nm.

Overall, the light source 1 can be used in selective drug activation and the effective monochromaticity of the output enables:

1. selection of biochemical absorption bands
2. selective targeting of tissue
3. variation of optical penetration.

It is envisaged that the light source 1 could be developed for monofilament fibre delivery to treat internal carcinomas with PDT and the output of the light source could be pulsed to minimise thermal effects for treatment of Portwine stains and tattoos.

In summary, the present invention provides a high intensity incoherent light source which combines the advantages of a laser (i.e. directional monochromatic and intense beam) with the advantages of lamp technology (i.e. low costs, simple design with reliability and a very broad tuning range). Thus, a portable device can be constructed which includes a fibre optic delivery system, said device being useful in a wide range of applications, in particular medical applications (both medical and therapeutic) such as in photodynamic therapy, hyperthermia, dermatological treatment such as removal of portwine and tattoo stains. Additionally, it is possible that the unit could be utilized in the area of diagnostics, although it has not been developed primarily for this. Thus, the present invention provides a light source yielding sufficient power within a narrow bandwidth suitable for PDT in addition to rendering the light deliverable via an optical fibre.

The fibre bundle 15 may be arranged to deliver a ½ watt of light with steep-sided 25 nm FWHM bandwidth to a patient directly or via a special purpose 2-lens collimating/focusing beamprobes or light conduits.

The output power of the light source will usually be at least in the order of 100 mW/cm$^2$.

Still further according to the present invention there is provided a high intensity incoherent or non-laser light source comprising a lamp, a (bandpass) filter and focusing means arranged to yield a monchromatic output beam of intensity greater than 0.075 watts per square centimetre which is tunable in the range of 250 to 1100 nm and which is preferably deliverable by a fibre optic bundle to a point of action.

It is to be understood that the scope of the present invention is not to be unduly limited by the particular choice of terminology and that a specific term may be replaced by any equivalent or generic term. Further it is to be understood that individual features, method or functions related to light source might be individually patentably inventive. In particular, any disclosure in this specification of a range for a variable or parameter shall be taken to include a disclosure of any selectable or derivable sub-range within that range and shall be taken to include a disclosure of any value for the variable or parameter lying within or at an end of the range. The singular may include the plural and vice versa.

What is claimed is:

1. A method of in vitro photodynamic therapy, said method comprising introducing a photodynamic drug into cancer cells and delivering non-laser light from an incoherent or non-laser light source of a sufficient intensity to kill said cancer cells, said incoherent or non-laser light source comprising a high intensity lamp, a bandpass filter and focusing structure arranged to focus a light beam from the lamp, said light beam having an output intensity greater than 0.075 watts per square centimeter and a bandwidth in the range 0 to 30 nm.

2. A method as claimed in claim 1 in which the non-laser light is focused sufficiently so that light can be delivered by way of an optical fiber means or bundle.

3. A method as claimed in claim 1 wherein said high intensity lamp is an arc lamp.

4. A method of in vitro photodynamic therapy, said method comprising introducing a photodynamic drug into cancer cells and delivering non-laser light from an incoherent or non-laser light source having a sufficient intensity to kill said cancer cells, said incoherent or non-laser light source comprising a high intensity arc lamp, a bandpass filter and focusing structure arranged to focus a light beam from the lamp, said light beam having an output intensity greater than 0.075 W/cm$^2$ and a bandwidth in the range 0 to 30 nm.

5. A method as claimed in claim 4 in which the non-laser light is focused sufficiently so that light can be delivered by way of an optical fiber means or bundle.

* * * * *